United States Patent [19]
Hou

[11] Patent Number: 5,900,496
[45] Date of Patent: May 4, 1999

[54] MICROBIAL PRODUCTION OF A NOVEL COMPOUND 7,10-DIHYDROXY-8-OCTADECENOIC ACID FROM OLEIC ACID

[75] Inventor: Ching T. Hou, Peoria, Ill.

[73] Assignee: The United States of America as represented by the Secretary of Agriculture, Washington, D.C.

[21] Appl. No.: 08/665,600

[22] Filed: Jun. 18, 1996

Related U.S. Application Data

[63] Continuation-in-part of application No. 07/496,577, Mar. 21, 1990, abandoned.

[51] Int. Cl.$^6$ .................................................. C07C 51/00
[52] U.S. Cl. ......................... 554/124; 554/213; 554/219; 435/132; 435/134; 435/874; 435/875
[58] Field of Search ..................................... 554/219, 124, 554/213; 435/874, 875, 132, 134

[56] References Cited

PUBLICATIONS

Parra et al, Tenside Surf. Det., vol. 27, 1990.
Chemical Abstract, vol. 115, #3, p. 635, 1991, 27719w.
E. Mercade et al., "New Surfactant Isolated from Pseudomonas 42A2," J. Amer. Oil Chem. Soc. 65(12): 1915–1916 (Dec. 1988).

J. L. Parra et al., "Studies of Biosurfactants Obtained from Olive Oil," Tenside Surf. Det. 27(5): 302–306 (1990).

J. L. Parra et al., "Studies of Biosurfactants from Olive Oil," Chem. Abstr. 114: 485z (1991).

Maurice Naudet et al., "Various Allyl Hydroxylated Derivatives of the Octadecenoic Chain," manuscript in process, unnamed journal.

*Primary Examiner*—Gary Geist
*Assistant Examiner*—Deborah D Carr
*Attorney, Agent, or Firm*—M. Howard Silverstein; Curtis P. Ribando; John D. Fado

[57] ABSTRACT

A strain of *Pseudomonas Sp.* bacterium (NRRL B-18602) has been discovered which is capable of converting oleic acid to the novel compound, 7,10-dihydroxy-8-octadecenoic acid (DOD). The production of DOD is unique in that it involves a hydroxylation at two positions and a rearrangement of the double bond of the substrate molecule. The new multifunctional, long-chain aliphatic acid has potential utility as a plasticizer and as a source of intermediates in the synthesis of specialty chemicals.

2 Claims, No Drawings

MICROBIAL PRODUCTION OF A NOVEL COMPOUND 7,10-DIHYDROXY-8-OCTADECENOIC ACID FROM OLEIC ACID

This application is a continuation-in-part of application Ser. No. 07/496,577, filed Mar. 21, 1990, now abandoned.

BACKGROUND OF THE INVENTION

1. Field of the Invention

Several vegetable oils produced mainly for edible use also find industrial applications. For example, soybean oil can be converted into alkyd resins for protective coatings, plasticizers, dimer acids, surfactants, and other products. Oleic acid is one of the most common fatty acids in vegetable oils. This invention relates to the fermentative conversion of oleic acid into a multifunctional, long-chain aliphatic acid with potential utility as a plasticizer and as a source of intermediates in the synthesis of specialty chemicals.

2. Description of the Prior Art

Several microbial/enzymic approaches for modifying agricultural oils or fats have been reported in recent years, including commercial application of lipases for fat splitting [Brockerhoff et al., In Lipolytic Enzymes, Academic Press, New York (1974)]. *Nocardia corallina, Pseudomonas sp.,* and *Puccinia graminis* are known to biosynthesize epoxy groups [Furuhashi et al., Eur. J. Appl. Microbiol. Biotechnol. 12: 39–45 (1981); Nihaus et al., J. Am. Chem. Soc. 89: 4227 (1967); Powell et al., Lipids 2: 172 (1967)]. Oleic acid serves as substrate for Pseudomonas and *P. graminis* to form 9,1-epoxy stearic acid. The cytochrome p-450 system from *Bacillus megatherium* appears to serve as a common enzyme for both epoxidation and hydroxylation of a variety of monounsaturated fatty acids [Ruettinger et al., J. Biol. Chem. 256: 5728–5734 (1981)]. Marsh et al., [Biochem. Biophys. Acta 60: 32 (1962)] show that yeast biosynthesizes hydroxy stearic acid from stearic acid. Microbial conersion of oleic acid to 10-hydroxystearic acid has been reported by Wallen et al. [Arch. Biochem. Biophys. 99: 249–253 (1962)]. They teach that a Pseudomoned isolated frcm a fatty material hydrates oleic acid at the double bond with a 14% yield. Litchfield et al. (U.S. Pat. No. 4,582,804) disclose that *Rhodococcus rhodochrous* converts oleic acid to 10-hydroxystearate and minor amounts of 10-keto-stearic acid. Kritala et al. [Appl. Microbiol. Biotechnol. 32:299–304 (1989)] have identified several microorganisms that hydrate oleic acid to 10-hydroxystearic acid at greater than 90% yield.

SUMMARY OF THE INVENTION

We have now discovered a novel multifuctional long-chain aliphatic fatty acid with potential utility as a plasticizer and as a source of intermediates in the synthesis of specialty chemicals. The new compound is 7,10-dihydroxy-8-octadecenoic acid (DOD). It is produced from oleic acid by the action of a new strain of a *Pseudomonas aeruginosa* bacterium. The production of DOD is unique in that it involves a hydroxylation at two positions and a rearrangement of the double bond of the substrate molecule. The structure of DOD has been determined instrumentally.

In accordance with this discovery, it is an object of the invention to introduce DOD as a novel chemical compound having potential utility as a plasticizer and as a source of intermediate compounds in the synthesis of specialty chemicals.

It is also an object of the invention to provide a method for proucing DOD by microbial fermentation or by enzyme biosynthesis.

Another object of the invention is to provide a new microorganism that can convert oleic acid to DOD.

It is also an object of the invention to provide a potential industrial chemical that is generated from natural renewable resources.

Other objects and advantages of this invention will become readily apparent from the ensuing description.

DETAILED DESCRIPTION OF THE INVENTION

The bacterium for use herein is a strain of *Pseudomonas aeruginosa,* isolated from a hog-farm pond near Morton, Ill. This isolate, referred to as *P. aeruginosa* PR3, is a motile, short rod-shaped, Gram-negative bacterium. It has multiple polar flagellae and is oxidase-positive. This strain grows aerobically but can not grow under anaerobic conditions. It forms white smooth colonies on agar and produces no water-soluble pigment. The invention strain has been deposited under the Budapest Treaty in the Agricultural Research Culture Collection (NRRL) in Peoria, Ill., and has been assigned Acession Number NRRL B-18602. For purposes of this invention, any isolate of this bacterium having all the identifying characteristics of NRRL B-18602, including subcultures thereof, would be effective.

The bacteria of the invention my be cultivated by any conventional meanss under any convenient aerobic conditions that promote their growth. Glucose, glycerol, and oleic acid can serve as carbon source for cell growth. The bacteria will grow over a wide pH range of at least pH 5–9, with the preferred range being about pH 6–7.

Under suitable cultivation conditions, the subject bacteria will convert oleic acid to DOD. Of the three carbon sources listed above, conversion is best when the cells are grown on glucose, though oleic acid by itelf is a suitable carbon source. Conversion does not seem to occur when the sole carbon source is glycerol. Conversion takes place over the pH range of about 5.5–8.5 and at temperatures of about 15–40° C. The preferred conditions for DOD production are pH 6.5–7.5 and a temperature of about 30° C. It is usually desirable to allow some time (preferably 36–48 hours) for the development of a new culture before bioconversion of oleic acid is initiated. Maximum production of DOD occurs about 48 hours after initiation, as illustrated in Example 4, below.

Upon completion of the fermentation, the reaction products are extracted from the culture broth with a nonpolar solvent or a combination of nonpolar solvents, preferably ethyl acetate and diethyl ether, and the solvents are removed from extracted material by evaporation. Separation and purification of DOD from the crude extract can be effected by the use of conventional techniques inclidomg. for example, countercurrent distribution (CCD), column chromatography (CC), high-performance liquid chromatography (HPLC), and thin-layer chromatography (TLC). In the prefereed eboient of the invention, we have successfully employed differential solvent extraction and silica gel column chromatography to afford pure DOD as a white powder. While not desiring to be limited thereto, the details of the separation procedure are illustrated in Example 2, below.

In an alternate embodiment of the invention, oleic acid can be converted to DOD in a cell-free enzyme preparation. We have found that DOD biosynthesis enzymes are loosely bound to the surface of *P. aeruginosa* PR3 cell membrane. These soluble surface enzymes can be removed by means of washing with a suitable buffer such as 0.05 M potassium phosphate buffer at pH 7.0 and separating them from the cells by centrifugation or the like. The cell-free enzyme preparation contains the DOD biosynthesis enzymes and not DOD degrading (metabolizing) enzymes which tend to reduce the yield of DOD in whole cell culture.

It is envisioned that the recovered DOD may have utility in the food and drug industries and as a plasticizer for improving the properties of rubbers and resins. It may also serve as a source of intermediate compounds for the synthesis of specialty chemicals including compounds such as alpha-hydroxy acid, which is imported by the United States.

The following examples are intended only to further illustrate the invention and are not intended to limit the scope of the invention which is defined by the claims.

EXAMPLE 1

Isolation and Culture of Bacteria

P. aeroginosa PR3 bacterial strain NRRL B-18602 was isolated by enrichment culture method from a hog-farm pond near Morton, Ill. Cultures were maintained on plate or agar slant with a medium of the following composition (per liter): 4 g glucose, 10 g $(NH_4)_2HPO_4$, 2 g $K_2HPO_4$, 0.5 g yeast extract, 0.5 g $MgSO_4.7H_2O$, 0.01 g $FeSO_4.7H_2O$, 0.008 g $MnSO_4.H_2O$, 0.014 g $ZnSO_4.7H_2O$, 0.01 g nicotinic acid, 15 g agar, and sufficient dilute phosphoric acid to adjust pH to 7.0. The same medium, without agar, was used at 30° C., for aerobic growth of bacteria and production of DOD.

EXAMPLE 2

Isolation, Purification, and Characterisation of DOD

A culture of NRRL B-18602 was grown aerobically at 30° C. in a 5-1 Fernbach flask containing 1 l of the medium of Example 1 with shaking at 150 rpm for 2 days. Oleic acid (0.8 ml) was added to the culture, and shaking at 150 rpm was resumed for another 2 days at 30° C. At the end of the reaction, the culture broth was acidified to pH 2 with 6 N hydrocloric acid to achieve thorough extraction. The broth was then extracted with an equal volume of ethyl acetate. The aqueous phase was again extracted with an equal volume of diethyl ether. The solvent was removed from the combined extracts with a rotary evaporator.

The solvent-free extracted material was partioned between hexane:acetonitrile (30 ml:30 ml). White material which appeared at the interface of these solvents was carefully collected and washed twice with hexane. The dried white material (95 mg) was found by TLC to be homogeneous (Rf 0.34). This White solid was methylated with diazomethane and analyzed by gas-liquid chromatography (GC). The methyl esters (1–2 µl), dissolved in diethyl ether, were injected into a "Hewlett Packard 5850" gas chromatograph that was equipped with a flame ionization detector, a "Supelco SPB" capillary column (15 m, i.d. 0.32 mm, 0.25 µm thickness) and a "Hewlett Packard 3392A" integrator. GC was run isothermally at 200° C. The major peak, having 97% purity, appeared at 19.93-min. retention time.

The acetonitrile fraction, which contained the major reaction product, was washed once with hexane and then evaporated to dryness in a rotary evaporator. The solid residue was dissolved in diethyl ether and separated on a silica gel G column (35 cm×2.2 cm i.d.) which had been pre-equilibrated with diethyl ether. The column was washed with 200 ml of ether and then eluted with ether:methanol (70:30 v/v). Five-milliliter fractions were collected and assayed by TLC. Fractions containing the main reaction product were combined and evaporated to dryness. The solid residue was washed with hexane and dried under nitrogen to 250 mg of a white powder. TLC and GC analyses of this white powder showed that the material was identical to that obtained previously with solvent partitioning. The melting point of this white powder was 64° C.

THE white powder (3 mg) was methylated with diazomethane and analyzed by GC-MS (Table I). The major component had an apparent molecular weight of 328, corresponding to a dihydroxy, 18-carbon, monoene ester. This structure was confirmed by GC-MS of the trimethylsilyl (TMS) derivative of the methylated compound, which incorporated two TMS groups for a molecular weight of 472, and by CI GC-MS of the TMS derivative of the unmethylated sample, which incorporated three TMS groups and had a molecular weight of 530. The locations of the two hydroxy and the double bond were apparent from the fragments observed in the electron impact spectrum of the TMS derivative of the methylated product. Intense fragments, arising from cleavage alpha to the derivatized hydroxyl groups to give a fragment containing both TMS groups and the double bond, were observed at m/z 343 and 359. These fragments located the hydroxyl groups at C7 and C10, respectively, and the double bond between the two hydroxyl groups, at C8. Based on these GC-MS data, the reaction product is 7,1-dihydroxy-8-octadecenoic acid (DOD).

DOD was also subjected to proton and $^{13}C$ NMR analyses. Proton NMR of DOD showed the presence of the following resonance signals: —CH=CH— group at 5.63 ppm; two tertiary protons —CH—O— at 4.08 ppm; —$CH_2$—COOH at 2.32 ppm; methylene groups from 1.2 to 1.6 ppm and a —$CH_3$ group at 0.86 ppm. $^{13}C$ NMR confirmed the presence of the following groups: carbonyl at around 178 ppm; a $C_8,C_9$ double bond at 133.88 and 133.60 ppm; $C_7$ and $C_{10}$ hydroxyl carbons at 72.3 and 72.4 ppm; —$CH_2$— groups cover the range frm 22.6 to 37.1 ppm; and the terminal methyl carbon at 14.1 ppm.

IR analyses of DOD were obtained on a KBr disc. The presence of hydroxyl groups was indicated by the strong, broad absorption at the

TABLE I

MS Analysis of DOD and Derivatives
m/e (intensity)

Methylated DOD

EI41(90),43(100),55(87),57(88),59(22),69(46),71(37),81(35),
83(23),85(21),87(56),97(22),111(16),119(18),125(28),130(21),
137(17),141(28),157(18),165(19),183(16),197(9),199(9),
279(1),310(M-18⁺;0.5)

TMS derivative methylated DOD

EI73(100),119(15),147(18),155(14),165(12),179(12),215(13),
231(18),253(53),269(63),330(5),343(42),359(28),441(2),
457(M-15⁺;2)

TMS derivative of DOD

CI351(30),369(12),441(MH-90⁺;100),515(M-15⁺;2),531(MH⁺;1)

3400-$cm^{-1}$ region. Carbonyl absorption at 1712 $cm^{-1}$ indicated free carboxyl. The methyl ester of DOD was then analyzed as a thin film, which showed absorption for ester carbonyl at 1740 $cm^{-1}$. Thus, the structure is 7,10-dihydroxy-8-octadecenoic acid.

DOD is insoluble in hexane, slightly soluble in toluene and benzene, and soluble in diethyl ether, chloroform, ethyl acetate, acetone, methanol, and acetonitrile.

EXAMPLE 3

Effeat of Carbon Source for Cell Growth

Three cultures of NRRL B-18602 were grown, in accordance with the procedures of Example 2 except that the containers were 125-ml shake flasks, the amount of medium was 30 ml, glyceol was substituted for glucose in one experiment (Example 3B), oleic acid was substituted for glucose in another experiment (Example 3C), and the amont of oleic acid added to each 2-day-old culture was 0.4 ml. After the conversion, each broth was acidified and extracted by the procedures of Example 2, and the solvent-free extracted material was methylated with diazomethane and analyzed for DOD by quantitative GC using methyl palmitate as an internal standard. The results in Table II show that cells grown on glucose were the most active in converting oleic acid to DOD.

EXAMPLE 4

Effect of Conversion Time on DOD Production

The procedures of Example 3 were repeated except that glucose was the carbon source in all cultures, and the respective conversion times were as listed in Table III. The results in Table III show that the amount of product DOD in the culture media reached a maximum (71% conversion of oleic acid) after 48 hours of reaction. The decline in DOD content with further incubation indicates that the product is being metabolized by the bacterium.

EXAMPLE 5

Effect of pH on Cell Growth

Growth media were prepared in accordance with the procedures of Example 3 except that glucose was the carbon source in all the media, and the media were adjusted,

TABLE II

Effect of Carbon Source on Cell Growth

| Example | Carbon Source | DOD produced (mg) |
|---|---|---|
| 3A | glucose | 220 |
| 3B | glycerol | 0 |
| 3C | oleic acid | 120 |

TABLE III

Effect of Conversion Time on DOD Production

| Example | Conversion Time (hour) | DOD Produced (mg) |
|---|---|---|
| 4A | 0 | 0 |
| 4B | 12 | 60 |
| 4C | 24 | 135 |
| 4D | 36 | 190 |
| 4E | 48 | 254 |
| 4F | 60 | 150 | respectively, with either 1 N sodium hydroxide or 1 N hydrochloric acid to one of the pH values listed in Table IV before inoculation with the bacterium. Table IV reports the yield of cells after shaking for 2 days at 30° C. The results show that pH 6–7 is optimum for cell growth.

EXAMPLE 6

Effect of pH on DOD Production

The procedures of Example 4 were repeated except that after cell growth at pH 7, the cultures were adjusted, respectively, with either 2 N sodium hydroxide or 3 N hydrochloric acid to one of the pH values listed in Table V, and all conversions proceeded for 2 days. Maximum yield of DOD occurred at pH 7.0 (Table V).

EXAMPLE 7

Effect of Temperature on DOD Production

The procedures of Example 3 were repeated except that glucose was the carbon source in all cultures, and the respective temperatures during oleic acid (0.2 ml) conversion were as listed in Table VI. The results in Table VI show that the temperature optimum for the production of DOD is about 30° C.

EXAMPLE 8

Enzyme Biosynthesis of DOD

One liter of 2-days old *Pseudomonas aeruginosa* PR3 (NRRL B-18602) culture broth was centrifuged at 10,000×g for 30 min at 4° C. to precipitate the cells. The cell pellet was resuspended in a 200 ml 0.05M potassium phosphate buffer (pH 7.0), stirred for 10 min and then centrifuged. The supernatant fraction which contained enzymes was used in the following experiment.

One ml substrate oleic acid was added into a 100 ml cell-free enzyme fraction and the mixture was incubated for two days at 30° C. on a 250 rpm shaker. At the end of the incubation, the mixture was acidified to pH 2 and extracted twice with an equal volume of diethyl ether and then ethyl acetate. The organic solvent extracts were combined and the solvent was removed to obtain crude product DOD. The amount of DOD was analyzed by gas chromatography. The yield was 93%.

It is understood that the foregoing detailed description is given merely by way of illustration and that modification and variations may be made therein without departing from the spirit and scope of the invention.

TABLE IV

Effect of pH on Cell Growth

| Example | pH | Concentration of Cells (mg/ml)[a] |
|---|---|---|
| 5A | 5.0 | 1.0 |
| 5B | 5.5 | 1.2 |
| 5C | 6.0 | 1.6 |
| 5D | 6.5 | 1.6 |
| 5E | 7.0 | 1.6 |
| 5F | 7.5 | 1.5 |
| 5G | 8.0 | 1.4 |
| 5H | 9.0 | 1.2 |

[a]Based on optical density measurements at 600 nm.

TABLE V

Effect of pH on DOD Production

| Example | pH | DOD produced (mg) |
|---|---|---|
| 6A | 5.5 | 15 |
| 6B | 6.0 | 50 |
| 6C | 6.5 | 160 |
| 6D | 7.0 | 230 |
| 6E | 7.5 | 120 |

TABLE V-continued

Effect of pH on DOD Production

| Example | pH | DOD produced (mg) |
|---|---|---|
| 6F | 8.0 | 30 |
| 6G | 8.5 | 5 |

TABLE VI

Effect of Temperature on DOD Production

| Example | Temperature (° C.) | DOD Produced (mg) |
|---|---|---|
| 7A | 15 | 4 |
| 7B | 20 | 15 |
| 7C | 25 | 64 |
| 7D | 30 | 135 |

TABLE VI-continued

Effect of Temperature on DOD Production

| Example | Temperature (° C.) | DOD Produced (mg) |
|---|---|---|
| 7E | 35 | 70 |
| 7F | 40 | 5 |
| 7G | 45 | 0 |

We claim:

1. A method for producing 7,10-dihydroxy-8-octadecenoic acid comprising incubating oleic acid in the presence of soluble surface enzymes recovered from a culture of *Pseudomonas aeruginosa* isolate PR3 having accession number NRRL B-18602.

2. The substantially pure *Pseudomonas aeruginosa* isolate PR3 having accession number NRRL B-108602.

* * * * *